United States Patent [19]

Ranford

[11] Patent Number: 4,950,241

[45] Date of Patent: Aug. 21, 1990

[54] DISPOSABLE SYRINGE

[75] Inventor: Alan B. Ranford, St. Louis, Mo.

[73] Assignee: Sherwood Medical Company, St. Louis, Mo.

[21] Appl. No.: 290,494

[22] Filed: Dec. 27, 1988

[51] Int. Cl.$^5$ .............................................. A61M 5/00
[52] U.S. Cl. ..................................... 604/110; 604/195
[58] Field of Search ............... 604/195, 198, 263, 110, 604/187, 207, 220, 246

[56] References Cited

U.S. PATENT DOCUMENTS

| 187,031 | 2/1877 | McMorries . | |
|---|---|---|---|
| 2,617,359 | 11/1952 | Van Horn et al. | 102/92 |
| 2,722,215 | 11/1955 | Stig-ake Dahlgren . | |
| 2,880,723 | 4/1959 | Adams . | |
| 3,306,290 | 2/1967 | Weltman . | |
| 3,426,448 | 2/1969 | Sarnoff | 35/17 |
| 3,889,673 | 6/1975 | Dovey et al. . | |
| 3,890,971 | 6/1975 | Lesson et al. . | |
| 4,026,287 | 5/1977 | Haller . | |
| 4,034,755 | 7/1977 | Schultz . | |
| 4,356,822 | 11/1982 | Winstead-Hall . | |
| 4,425,120 | 1/1984 | Sampson et al. | 604/198 |
| 4,643,199 | 2/1987 | Jennings, Jr. et al. | 128/763 |
| 4,643,200 | 2/1987 | Jennings, Jr. | 128/763 |
| 4,664,654 | 5/1987 | Strauss | 604/198 |
| 4,666,435 | 5/1987 | Braginetz | 604/198 |
| 4,675,005 | 6/1987 | DeLuccia | 604/110 |
| 4,692,156 | 9/1987 | Haller | 604/195 |
| 4,747,830 | 5/1988 | Gloyer et al. | 604/110 |
| 4,790,822 | 12/1988 | Haining | 604/110 |

Primary Examiner—John D. Yasko
Attorney, Agent, or Firm—Andrew J. Beck; Montgomery W. Smith; Charles Smith

[57] ABSTRACT

A retractable needle syringe is disclosed which includes an elastomeric anchor connected at the distal end of a syringe barrel with a needle connector releasably connected in the anchor and adapted to carry a needle cannula. A plunger with a piston is provided with a coupling member movable into coupling engagement with a coupling member on the needle connector to connect the needle connector with the plunger. A seal on the piston prevents fluid from flowing out of the cannula when coupling engagement between the piston rod and the needle connector is effected. The coupling member on the plunger moves a portion of the anchor away from the needle connector to reduce the force necessary to remove the needle connector from the anchor. The plunger is moveable proximally in the barrel to move the needle connector and a needle connected thereto into the barrel. The plunger rod has a weakened portion to permit manual breakage of the rod.

47 Claims, 2 Drawing Sheets

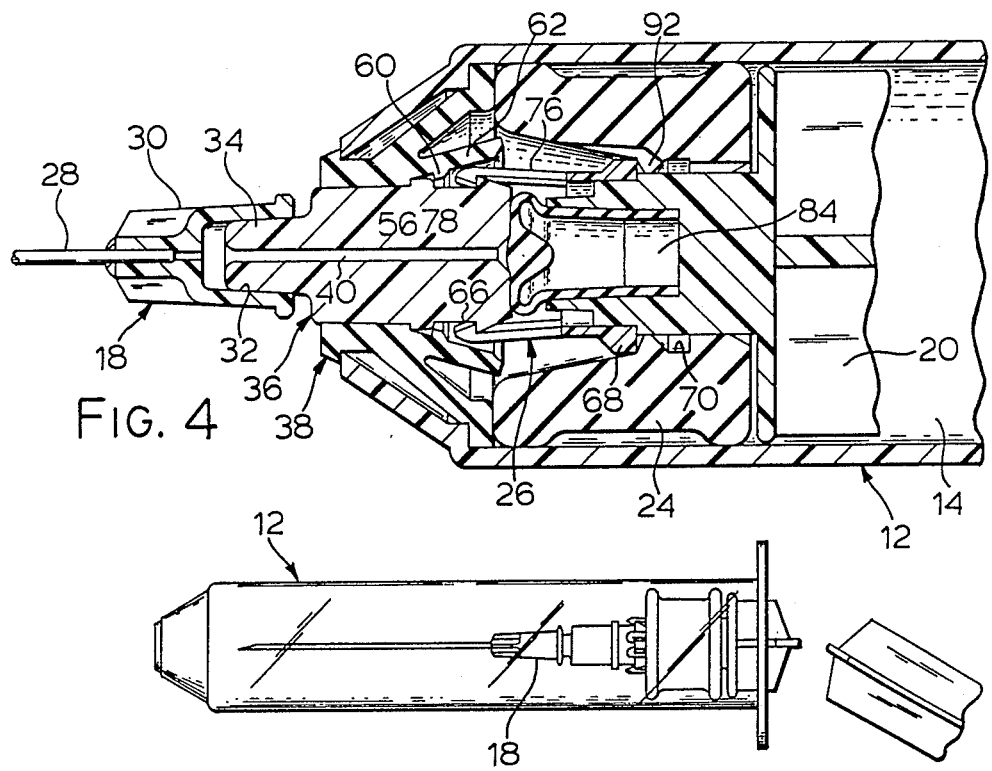
FIG. 4
FIG. 5
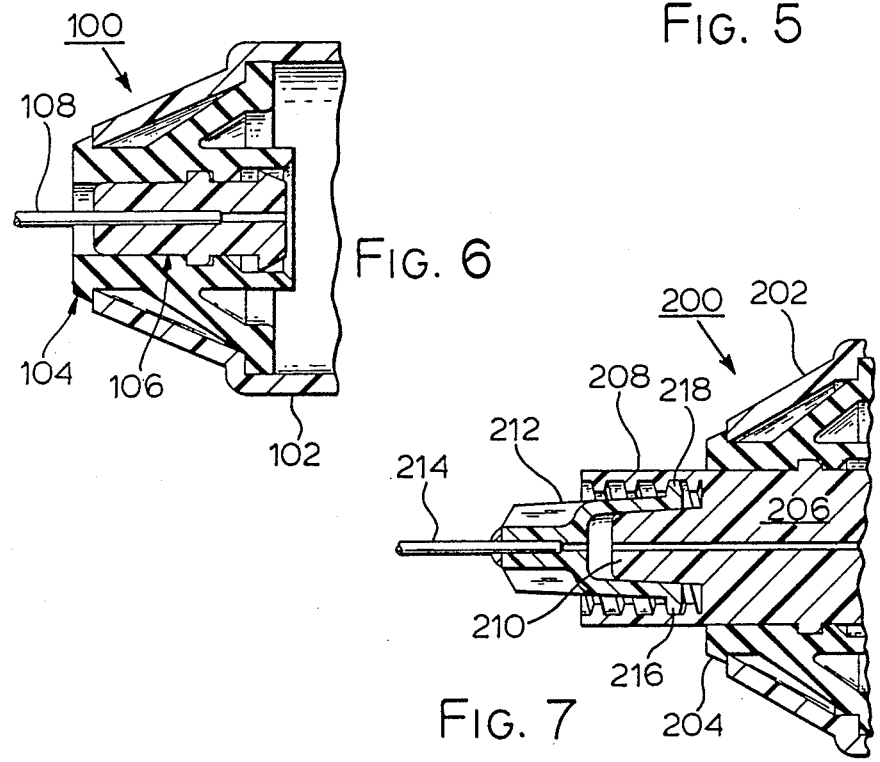
FIG. 6
FIG. 7

DISPOSABLE SYRINGE

FIELD OF THE INVENTION

This invention relates to disposable syringes, and more particuluary to a disposable syringe of the type having a retractable cannula.

BACKGROUND OF THE INVENTION

As is well known, the use of conventional hypodermic syringes presents a potential health hazard to those employing the syringe as well as to any other health care worker that may handle syringes after use. It is not rare that the person administering an injection is inadvertently stuck by the pointed end of the cannula after withdrawal of the cannula from the patient or during subsequent handling or disposal of the used syringe. For example, this might occur where a sheath is placed over the cannula of a conventional syringe preparatory to the disposal of the syring. Such occurrences may also happen because of inadvertent mishandling or dropping of the syringe even where good disposal practices are normally used. Such occurrences can of course result in the spread of infectious disease, such as Aquired Immune Deficiency Syndrome (AIDS) or hepatitus.

A number of syringe constructions have been proposed in an attempt to prevent or reduce the number of occurrences of health care personnel being inadvertently stuck by contaminated needles.

In U.S. Pat. No. 4,026,287, a syringe is provided with a needle cannula fixed to the forward end portion of the syringe barrel, which end portion is integral with the barrel but made fragile to break away from the barrel. The end of the plunger upon completion of an injection, is locked to the fragile end portion of the barrel to break the end portion away from the barrel and withdraw the end portion and the needle into the syringe barrel as the plunger rod is retracted. In order to connect the plunger rod with the break-away portion of the barrel, the distal end of the plunger rod is shaped to engage a coupling formed on the inner side of the barrel end portion. Because the plunger must be moved forward when coupling it to the barrel end portion, the residual injection fluid will generally undesireably squirt out the end of the needle. Also, it appears that the breaking of the syringe end portion might be relatively difficult and therefore tend to even contribute to the danger that the person disposing of the syringe will be inadvertently stuck by the needle during efforts to break the syringe end portion. Such a barrel could not practically be made of the commonly used plastic, polypropylene since the breaking away of the end portion of a polypropylene barrel would be very difficult.

A syringe is shown in U.S. Pat. No. 4,692,156 that has a needle secured in the foward end of a syringe barrel by means of a deformable mounting post. The proximal end of the needle is provided with a coupling surface which is engaged by a distally extending end portion of the piston which, after aspiration of the fluid in the barrel, is locked onto the needle. Upon retraction of the piston rod, the needle and the mounting post are retracted into the barrel. With this construction, forward movement of the piston to lock onto the needle will also generally result in fluid being squirted out the tip of the needle. Also, since the mounting post must be sufficiently rigid to hold the needle in its normally exposed position during normal use of the syringe and yet pass through the syringe tip passage when the needle is retracted, retraction of the needle into the barrel may be relatively difficult.

Another type of safety syringe is shown in U.S. Pat. No. 4,666,435. This device utilizes a generally cylindrical shield which receives the syringe barrel and is slidable relative to the syringe so that the shield surrounds the needle after use of the syringe. This construction requires a relatively large shield and complexshaped cooperating features molded on the inside of the barrel and outside of the shield which make the device relatively expensive.

SUMMARY OF THE PRESENT INVENTION

It is an object of the present invention to provide a syringe having a needle connector adapted to carry a needle which is retractable into the barrel of the syringe after use of the syringe which substantially obviates the above-memtioned undesirable features and problems.

A more specific object of the present invention is to provide a syringe in which a needle connector adapted to carry a needle is retractable into the syringe barrel after use wherein the needle connector is securely held in place during normal use of the syringe but which can be relatively easily and safely withdrawn along with a needle connected thereto into the syringe barrel for safe disposal of the syringe.

Still another object of the present invention is to provide a syringe in which a needle connector adapted to carry a needle is retractable into the barrel of the syringe after use by actuating the syringe plunger into locking engagement with the needle and retracting the plunger to retract the needle connector into the barrel wherein actuation of the plunger into locking engagement does not result in a discharge of fluid out of the needle.

In accordance with one aspect of the present invention, a syringe is provided which includes a syringe barrel, a plunger slidable in the barrel, a resilient anchoring member at the distal end of the syringe barrel, and a needle connector releasably connected to the anchoring member and adapted to hold a needle. The plunger has a coupling member at its distal end which is movable into coupling engagement with the needle connector and is movable to release the needle connector from the anchoring member and move the connector into the barrel.

In accordance with another aspect of the invention, a syringe is provided that includes a barrel and a plunger slidable in the barrel. A needle connector for holding a needle is normally secured in a resilient anchor member at the distal end of the barrel. The anchor member includes an abutment normally engaging the needle connector. The plunger includes a coupling member which is movable to disengage the abutment from a portion of the needle connector and to move distally into coupling engagement with the needle connector. The plunger is thereafter movable proximally for removing the connector from the anchor member and moving it into the barrel.

In accordance with another aspect of the present invention, a syringe is provided which includes a barrel, an elastomeric anchor releaseably holding a needle connector adapted to carry a needle cannula, and a plunge having a coupling member at the distal end thereof which is movable into coupling engagement with a coupling member on the needle connector for moving the connector from the anchor and a needle connected to the connector into the syringe barrel.

In accordance with another aspect of the present invention, a needle-retractable syringe includes a barrel, a connector at the distal end of the barrel for carrying a needle, and a plunger slidable in the barrel and actuatable into locking engagement with the connector for retracting the connector into the barrel. Seal means is provided for preventing fluid flow from the barrel to the connector during actuation of the plunger into locking engagement with said connector.

In accordance with still another aspect of the present invention, a needle-retractable syringe is provided which includes a barrel, a needle connnector, and a plunger having a piston slidable in the barrel. The plunger is actuatable into locking engagement with the needle connector for retracting the needle connector into the barrel. Vent means are provided which openable to substantially prevent a negative pressure in the barrel as a result of proximal movement of the piston during retractile movement of the plunger subsequent to the locking engagement with the needle connector.

These as well as other objects and advantages of the present invention will become apparent from the following detail description and accompanying drawings.

BRIEF DESCRIPTION OF THE DRAWINGS

FIG. 4 is a cross-sectional view similar to FIG. 2 but with the plunger coupled to the needle connector;

FIG. 5 is a side elevational view of the syringe of FIG. 1 but with the needle connector and needle retracted into the syringe barrel and the plunger rod broken;

FIG. 6 is a longitudinal cross-sectional view of the distal end portion of a syringe in accordance with a modified embodiment of the present invention; and FIG. 7 is a cross-section of the distal end portion of a syringe in accordance with another modified embodiment of the invention.

DETAILED DESCRIPTION OF THE PREFERRED EMBODIMENTS

Figure 1:
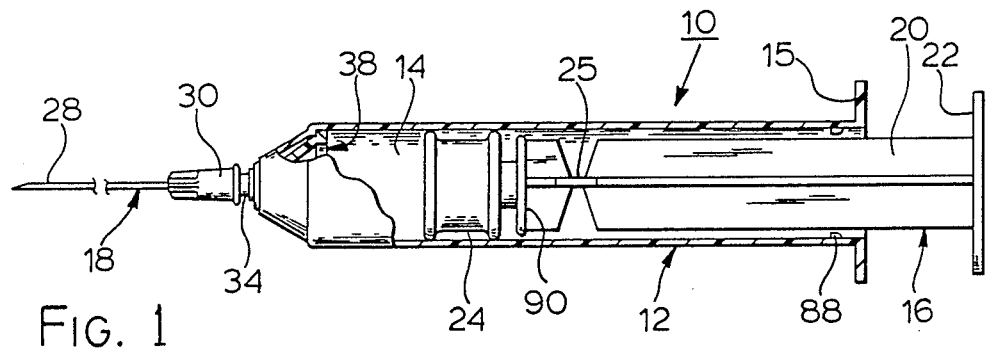
FIG. 1 is a side elevational view, with a portion broken away, of a syringe in accordance with a preferred embodiment of the present invention.

Referring now to the drawings, and more particularly to FIG. 1, there is shown a hypodermic syringe indicated generally at 10 which is in accordance with a preferred embodiment of the present invention. Syringe 10 is shown including a generally cylindrical syringe barrel 12 having a bore 14 open at the proximal and distal ends, and a plunger 16 reciprocally slideable in bore 14. The barrel is provided with a radially outwardly extending finger flange 15 at its proximal end. A needle assembly 18 is connected at the distal end of the barrel 12 for the administration of an injectable fluid or for extracting a fluid, such as blood, from a patient.

Figure 2:
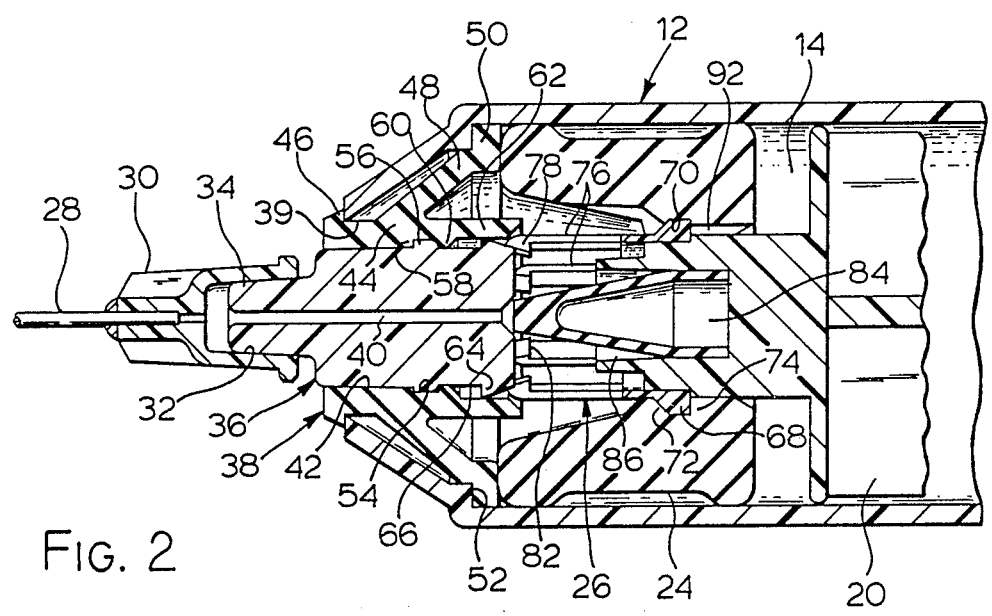
FIG. 2 is a longitudinal cross-sectional view on an enlarged scale of the distal end portion of the syringe of FIG. 1 but with the piston at the distal end of the syringe barrel.

The plunger 16 includes a rod 20 having an integral radially outwardly extending flange 22 at the proximal end and a plunger tip or piston 24 at the distal end. The piston 24 is made of conventional elastomeric material such as a suitable rubber which is sealingly slidable along wall of bore 14. The rod 20 is cruciform in cross-section and is provided with a frangible or weakened portion 25 proximally spaced from but closer to the distal end of the rod than to the proximal end thereof. Also connected to the distal end of rod 20 and as seen in FIG. 2, is a coupling member 26 to be fully discussed hereafter.

The needle assembly 18 is shown including a needle cannula or hypodermic needle 28 fixed to a needle hub 30 having an inner female luer tapered connector surface 32. The luer tapered surface 32 is connected to a male, luer tapered connector 34 of a needle connector 36. The needle connector 36 is releasably connected to a needle anchor member 38 that is fixed to barrel 12 at the distal end thereof and which is shown extending through a distal end opening 39 of the barrel. The needle connector 36 has a fluid flow passage 40 normally connecting the needle cannula 28 in fluid communication with bore 14 on the distal side of piston 24. Needle connector 36 is generally circular in cross-section and formed of relatively rigid material such as a rigid plastic, for example, polypropylene.

The anchor 38 is a resilient member, preferably of an elastomeric material such as rubber or other elastomeric material. The anchor has a bore 42 extending through it and which frictionally receives the needle connector 36 in fluid tight sealing engagement to normally hold the needle connector in fixed relation to the syringe barrel 12 and prevent any pressurized fluid from flowing out of the barrel except through needle 28. The anchor 38 is shown for illustration as a single piece elastomeric bushing having a main central, generally cylindrical body portion 44 with the walls of bore 42 frictionally engaging the outer surface of needle connector 36. The anchor has an annular radially outwardly extending flange 46 engaging the distal end surface of the barrel 12 which is integrally connected to body portion 44. The anchor 38 also has a generally conical portion 48 integral with body portion 44 and slightly spaced from the barrel to permit some flexing of the anchor for easier removal of the needle connector 36. There is also provided on the anchor an annular radially outwardly extending flange 50 integrally connected to the upper end of the conical portion 48 and engaging a shoulder or radially inwardly extending flange or wall 52 on the interior of the barrel. The flanges 46 and 50, and the conical portion 48 are sized to frictionally fix the anchor 38 at the distal end of barrel 12. If desired, the contacting surfaces of the anchor 38 and barrel 12 may be adhesively or otherwise bonded together.

The wall of bore 14 is provided with an annular groove 54 in the central portion 44 of the anchor which receives an annular, radially outwardly extending integral flange 56 on the needle connector 36 to normally positively secure or lock the needle connector in anchor 38 and normally prevent movement thereof in either proximal or distal directions. The groove 54 of the anchor has a pair of opposed annular walls 58 and 60 engaging the opposed sides of the connector flange 56, the wall 60 serving as a detent. The anchor 38 also includes a cylindrical, axially extending anchor release portion or skirt 62 connected to the wall or detent 60 and which extends closely over an annular radially outwardly extending abutment or flange 64 on the needle connector 36 adjacent the proximal end thereof. The abutment 64 has a distal side extending radially outwardly and a proximal side inclined distally upwardly from the proximal end of the connector to the outermost edge of the abutment. The radial flange 56 and abutment 64 which is spaced from the flange 56 define an annular groove 66 in connector 36 and into which the anchor wall 60 extends. The needle connector 36 is thus normally frictionally held in fixed relation to the anchor 38 and barrel 12 by the engaging outer walls of the connector 36 and the inner walls of the anchor bore 42 and with the complementary anchor groove 54 receiving the needle connector flange 56.

The needle latching or coupling member 26 is connected to the distal end of the plunger rod 20 such as by welding, or by an integral connection or bonding. The coupling member 26, as seen also in FIG. 3, includes a cylindrical portion 67 having a radially outwardly extending flange 68 at the proximal end which is shown in FIG. 2 disposed in a groove 70 in the inner wall of the piston 24. The piston groove 70 has opposed walls 72 and 74 engaging the opposed sides of flange 68. In the illustrated embodiment of FIG. 2, the opposed walls 72 and 74 normally help maintain the piston 24 in fixed relation to the rod 20.

Figure 3:
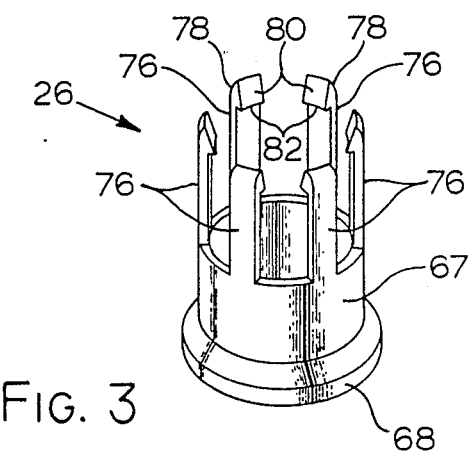
FIG. 3 is a isometric view of the coupling element of the plunger of FIG. 2 alone.

The coupling member 26, as best seen in FIG. 3, includes integral resilient latching members 76 shown for illustration as six like-shaped distally extending arms integrally connected with the cylindrical portion 67. At the distal end of each arm is a latch 78 having a inner distally outwardly inclined distal end surface 80 and a radially extending proximal latching or locking surface 82.

Connected also to the distal end of the plunger rod 20 within the coupling member 26 is a resilient seal or plug 84 preferably connected within an end recess 86 in the rod such as by an interference fit or by bonding. The plug 84 is preferable formed of rubber or other elastomeric material. The plug 84 has a length such that its distal end closes or is close to the proximal end of the passage 40 of the needle connector when the piston 24 contacts the flange 50 of anchor member 38, that is, when the piston is at its distal-most position in the barrel 12, the position shown in FIG. 2.

In operation, after the plunger 16 has been moved to its distal-most position after ejection of fluid from bore 14, such as after the injection of a medicament into a patient, the needle is removed from the patient and the plunger 16 is urged further distally forward causing the coupling member 26 to move into coupling or locking engagement with the needle connector 36 as shown in FIG. 4. During this actuating distal movement of plunger rod 20, the rod 20 and coupling member 26 move distally relative to piston 24 with the flange 68 of the coupling member 26 moving past the resilient piston wall 72. During this actuating movement, inclined surfaces 80 of the latches 78 on latch arms 76 slide upwardly on the inclined surfaces of the abutment 64 of the needle connector 36 with the latches 78 snapping into the groove 66 on the distal side of the coupling abutment 64 as shown in FIG. 4. In this condition, the coupling member 26 is securely coupled or locked to the needle connector 36.

During the actuating movement of the plunger 16, the coupling member 26 moves distally into coupling or locking engagement with the coupling abutment 64. The latches 78, as they move distally, move the anchor release portion 62 radially outwardly causing the detent wall 60 to substantially move away from or out of the groove 66 in the needle connector 36. Also, during this movement, the plug 84 seals the proximal end of the passage 40 in the connector 36 so that any residual fluid or liquid remaining in bore 14 cannot be forced into passage 40 and needle 28 by the fluid displacing distal movement of plunger rod 20 thereby preventing the squirting of fluid out of the needle during movement of the piston rod from the position shown in FIG. 1 to that shown in FIG. 4. The displacement of residual fluid during actuation of the plunger into locking engagemnt with needle connector will generally cause slight proximal displacement of the piston in the bore.

After plunger 16 is coupled to the needle connector 36 (FIG.4), the plunger is pulled proximally relative to barrel 12 thereby removing the connector 36 from anchor 38 and moving the connector and the needle assembly 18 into bore 14 of the barrel 12, the condition shown in FIG. 5. The piston 24 is moved close to the proximal end of the barrel 12 with the needle wholly within the bore 14. After the needle is fully retracted into the barrel, the barrel and plunger rod 20 may be hand grasped and then moved angularly relative to each other to break the rod at the frangible portion 25 as illustrated in FIG. 5. The disabled syringe 10 with the needle 18 retracted within the barrel can then be disposed of safely.

A piston stop 88 is shown in FIG. 1 on the wall of bore 14 spaced from the proximal end of the barrel to automatically stop the proximal movement of the plunger in the fully retracted position. The stop 88 is shown as an annular ring integral with the bore wall and protruding radially inwardly to engage an abutment on the rod 20 such as provided by an annular radial flange 90 adjacent the proximal side of the piston 24. The abutment 88 and flange 90 are preferably relatively located to engage each other when the frangible portion 25 is just proximal of the distal end of the barrel as indicated in FIG. 5.

A normally closed vent is shown in the form of a passage 92 extending axially across the piston 24 as seen in FIGS. 2 and 4. Passage 92 is shown as an axial groove on the radially inner wall of pistion 24 which connects with piston groove 70 and is normally obstructed by flange 68 of coupling member 26 (FIG. 2) for permitting normal operation of the syringe 10. During movement of piston rod 20 from its position in FIG. 2 to its actuated position in FIG. 4, the flange 68 moves from groove 70 to open the vent passage 92 and permit fluid or air flow from the proximal side of the piston to the distal side thereof to thereby allow the piston to move proximally in the bore 14 during retraction of the needle 28 into bore 14 without effecting a suction lock or negative pressure build-up while the needle connector 36 is being pulled through the anchor 38. Thus, the vent passage 92 and piston rod 20 with flange 68 serve as a valve to prevent a vacuum lock or negative pressure that, if permitted, would resist proximal movement of the piston during retraction of the needle into the barrel.

The resilient anchor 38 provides a good fluid tight seal between the inner walls of the bore 14 and the anchor as well as between the inner walls of the anchor and the outerwalls of the needle connector 36 so that even under high fluid pressure conditions that may be produced by movement of the plunger 16, fluid cannot leak out of the distal end of the barrel. While the anchor 38 tightly holds the needle connector 36 in place during normal use of the syringe, the pulling force required to remove the connector 36 from the anchor 38 and retract it and the needle 28 into the barrel 12 is relatively low. This is because the latches 78 remove or substantially remove the anchor detent wall 60 from the needle connector groove 66 prior to retraction of the needle connector. Also, because the seal 84 automatically sealingly closes the passage 40 in connector 36 during the distal movement of the plunger rod 20 during the coupling between the rod 20 and connector 36 as previously mentioned, the squirting out of medicament from the distal tip of the needle 28 and onto personnel and furnishings is avoided.

The embodiment of FIG. 6, illustrates a syringe 100 which is like syringe 10 of the embodiment shown in FIGS. 1–5 except that this syringe is of the "fixed needle" type, that is, a syringe having a needle connected to it during manufacture and which is not removable. The syringe 100 has a barrel 102 and an anchor member 104 respectively similar in construction to the barrel 12 and anchor member 36 of syringe 10. This syringe has a needle connector 106 similar to the needle connector 36 of syringe 10 except that the needle cannula, indicated at 108, is permanently fixed to the connector 106 for example, by an adhesive or insert molding. The construction and operation of syring 100 is similar to that of syringe 10. For example, a coupling member (not shown) which may be identical to member 26 of syrnge 10 and connected to the syringe piston rod not shown, can be coupled in similar manner to the needle connector 106 and then moved proximally to release it from the anchor 104 and move it and the needle 108 into the barrel 102.

Another modified embodiment is shown in FIG. 7 which is also similar in construction to syringe 10. A syringe 200 is shown including a barrel 202, an anchor member 204 secured in the distal end of the barrel, and a needle connector 206 releasably connected in the anchor member 204. In this embodiment the needle connector is integrally formed with a threaded luer lock skirt or collar 208 surrounding an integral luer tapered connector 210. A convention needle hub 212 is shown fixed to a needle cannula 214. The hub 212 has conventional ears or "threads", indicated at 216 and 218, which are shown threadedly received within the luer lock collar 208 with the luer connector 210 sealingly connected to the luer tapered hub 212 to connect the needle 214 in fluid communication with the bore of barrel 202. A coupling member like that of coupling member 26 of syringe 10 can be used to retract the connector 206 and needle 214 wholly within the barrel 202.

The complementary coupling members, for example, members 26 and 64 of FIG. 2, which are coupled together when actuated into locking engagement by the plunger rod, can be of various forms as long as the plunger rod can be coupled to the needle connector and move it into the barrel. The barrel and plunger rod may be made of a suitable hard plastic, for example, polypropylene.

As various changes can be made in the above-described construction without departing from the scope of the invention, it is intended that all matter contained in the above description and drawings be interpreted as illustrative and not in a limiting sense.

What is claimed is:

1. A syringe comprising: a barrel; a plunger slidable in said barrel; an elastomeric member fixed within said barrel at a distal end thereof and having an opening therethrough; needle connector means positioned in said opening of said elastomeric member and having a passage therethrough for connecting a needle cannula in fluid communication with said barrel; anchor means on said elastomeric member for retaining said needle connector means within said opening; coupling means on said needle connecter means and on said plunger for coupling said plunger to said needle connector means in response to predetermined movement of said plunger; and said anchor means providing for release of said needle connector means from said elastomeric member in response to said predetermined movement of said plunger to permit withdrawal of said needle connector means from said opening of said elastomeric member to within said barrel.

2. The syringe of claim 1 wherein said coupling means includes abutment means on one of said needle connector means or said plunger, and latch means on the other of said needle connector means or said plunger movable into locking engagement with said abutment means.

3. The syringe of claim 1 wherein said needle connector means is frictionally anchored in said elastomeric member.

4. A syringe comprising a barrel; a plunger slidable in said barrel; resilient anchor means connected to said barrel at the distal end thereof and having an opening therethrough; and needle connector means releasably anchored in said opening for connecting a needle cannula in fluid communication with said barrel, said needle connector means including first coupling means adjacent the proximal end thereof, said plunger including second coupling means adjacent the distal end thereof complementary to said first coupling means, said second coupling means being movable into coupling engagement with said first coupling means in response to predetermined distal movement of said plunger, said plunger being movable in the proximal direction subsequent to said coupling engagement to release said needle connector means from said anchor means and move said needle connector means into said barrel, said plunger including vent passage means extending between proximal and distal sides of said plunger, and means normally closing said vent passage means, said last named means and said vent passage means being relatively movable to open said vent passage means during said predetermined distal movement of said plunger.

5. The syringe of claim 1 wherein said elastomeric member has a portion thereof normally engaging a portion of said needle connector means to resist movement of said needle connector means into said barrel, and a portion of said coupling means is engageable with said portion of said elastomeric member to urge the same in a direction out of engagement with said portion of said needle connector means in response to said predetermined movement of said plunger.

6. The syringe of claim 4 wherein said plunger includes seal means for closing said passage through said needle connector means during said predetermined distal movement of said plunger.

7. The syringe of claim 1 wherein said plunger includes a rod having a frangible portion thereon which is manually fracturable.

8. The syringe of claim 7 wherein said plunger and said barrel have complementary abutment means for stopping proximal movement of said plunger at a point where said frangible portion of said rod is adjacent the proximal end of said barrel.

9. The syringe of claim 1 wherein said needle connector means includes a luer tapered connector at the distal end thereof for receiving the hub of a needle for connecting the needle to the barrel.

10. The syringe of claim 9 wherein said needle connector means includes a luer lock threaded collar surrounding said luer tapered connector for receiving thread means on the hub of a needle.

11. The syringe of claim 1 wherein a needle is connected to said needle connector means with a needle cannula of said needle in fluid communication with said barrel.

12. The syringe of claim 1 wherein said plunger includes seal means for closing said passage through said needle connector means during said predetermined movement of said plunger.

13. A syringe comprising: a barrel; a plunger slidable in said barrel; a needle connector releasably connected to said barrel at the distal end thereof and having a passage therethrough for connecting a needle cannula in fluid communication with said barrel; coupling means on said needle connector and on said plunger for coupling said plunger to said needle connector in response to predetermined movement of said plunger; and seal means at the distal end of said plunger for sealingly closing said passage during said predetermined movement of said plunger to prevent fluid flow from said barrel to said needle during said predetermined movement of said plunger.

14. The syringe of claim 13 wherein at least a portion of said seal means includes an elastomeric material.

15. A retractable needle syringe comprising a barrel having a bore open at proximal and distal ends thereof, a plunger reciprocally movable in said bore including a rod extending through the proximal open end of said bore, and resilient piston means connected to the distal end of said rod and sealingly slidable against the wall of said bore, resilient anchor means fixed in said bore adjacent the distal end thereof and extending through the distal open end of said bore, said anchor means having an opening therethrough, a needle connector having a passage therethrough for connecting a needle in fluid communication with said bore, said connector being releasably connected in said opening and having radial abutment means thereon adjacent to the proximal end thereof, and axially extending latching means connected to said rod at the distal end thereof having portions movable over said abutment means into latching engagement therewith to lock said connector to said rod in response to predetermined distal movement of said rod, said rod being movable in the proximal direction with said connector locked thereto move said connector from said anchor means and into said barrel.

16. The syringe of claim 15 wherein said connector has a second generally radially extending abutment thereon, and said anchor means includes an axially extending portion having a radially extending anchor abutment thereon normally disposed axially of and adjacent to said second abutment for retarding axial movement of said connector relative to said anchor means, said latching means being moveable into engagement with said axially extending portion of said anchor means to move said anchor abutment thereon in a general radial direction away from said second abutment during said predetermined movement of said rod to reduce the force necessary to move said connector from said anchor means.

17. The syringe of claim 16 further including resilient seal means in said bore adapted to close the proximal end of said passage during said predetermined distal movement of said rod.

18. The syringe of claim 17 wherein said seal means is connected to said rod at the distal end thereof.

19. The syringe of claim 15 wherein said rod and said latching means are distally movable relative to said pistion after said piston has reached its distal-most position in said bore.

20. The syringe of claim 19 wherein a portion of said portion means surrounds said latching means.

21. The syringe of claim 20 including an elastomeric seal connected to said rod in concentric relation with said latching means and said portion of said piston means and moveable to close said passage during said predetermined distal movement of said rod.

22. The syringe of claim 15 further including a needle cannula connected to said connector and moveable with said connector into said barrel.

23. The syringe of claim 22 wherein said connector includes a luer tapered connector at the distal end thereof adapted to receive a luer hub of a needle assembly.

24. The syringe of claim 22 wherein said connector includes a threaded luer lock collar at the distal end thereof adapted to threadedly receive a luer hub of a needle connector.

25. The syringe of claim 15 wherein said latching means includes a plurality of circumferentially disposed resilient latching arms each having a latch thereon movable into locking engagement with said abutment means on said connector.

26. The syringe of claim 15 wherein said plunger includes vent passage means between said piston and said plunger for connecting said bore on the distal and proximal sides of said piston in fluid communication, means on said rod normally closing said vent passage means, said last named means being movable in response to said distal movement of said rod to move said last named means relative to said vent passage means to open said vent passage means.

27. A retractable-needle syringe comprising a barrel, a plunger slidable in said barrel and having a piston thereon, connector means releasably connected to said barrel at the distal end thereof for carrying a needle, and a pair of coupling means respectively connected to said connector means and said plunger, said plunger being movable to effect locking engagement between said coupling means and movable proximally in said barrel to retract said connector means and said needle into said barrel, and valve means on said plunger preventing fluid passage between opposed sides of said piston during distal movement of said plunger and permitting fluid passage from the distal side to the proximal side of said piston during proximal movement of said plunger subsequent to said locking engagement between said coupling means.

28. The retractable-needle syringe of claim 27 wherein said plunger includes seal means for preventing fluid flow from said barrel to said connector means during movement of said plunger when effecting said locking engagement between said coupling means.

29. A method of retracting a needle into a barrel of a syringe comprising the steps of:
 providing a syringe barrel;
 providing a needle connector carrying a hypodermic needle and having a fluid flow passage therethrough between the lumen of the needle and the syringe barrel and a coupling member thereon;

providing an elastomeric member disposed at the distal end of the syringe barrel for supporting the needle connector;

providing a plunger with a coupling member thereon and seal means thereon;

moving the plunger distally in the syringe barrel for discharging fluid in the syringe barrel through the needle connector and the needle;

moving the plunger further distally to move the seal means to close the needle connector passage and to place the coupling members on the plunger and the needle connector into locking engagement; and moving the plunger proximally in the syring barrel to pull the needle and the needle connector into the syringe barrel.

30. A method of administering a fluid to a patient comprising from a syringe comprising the steps of:

moving a plunger distally within a barrel to fully discharge fluid from the barrel through a passage of a needle connected to a needle connector positioned at a distal end of the barrel; thereafter further moving the plunger distally with the barrel to couple the plunger to the needle connector and sealing the passage of the needle during at least a portion of said further moving step to prevent discharge of fluid from the barrel through the passage of the needle; and thereafter moving the plunger proximally within the barrel to retract the needle connector and needle within the barrel.

31. The method of claim 30 further comprising the step of:

releasing the needle connector from engagement with the distal end of the barrel with such further distal movement of the plunger.

32. A method of administering a fluid to a patient from a syringe comprising the steps of:

moving a plunger having a piston in slidable sealing engagement with the inside wall of a barrel distally within the barrel to fully discharge fluid from the barrel through a needle passage of a needle connected to a needle connector positioned at a distal end of the barrel; thereafter further moving the plunger distally within the barrel to couple the plunger to the needle connector and opening a vent passage between the space within the barrel distal of the piston and the space within the barrel proximal of the piston during at least a portion of said further moving step; and thereafter moving the plunger proximally within the barrel to retract the needle connector and needle within the barrel.

33. The method of claim 32 further comprising the step of:

sealing the needle passage during at least a portion of said further moving step to prevent discharge of fluid from the barrel through the needle passage.

34. The method of claim 32 further comprising the step of:

releasing the needle connector from engagement with the distal end of the barrel with such further distal movement of the plunger.

35. A syringe comprising:
a barrel;
a plunger slidable in said barrel;
needle connector means releasably retained in an opening at a distal end of said barrel and having a needle passage means therethrough for connecting a needle cannula in fluid communication with said barrel;

coupling means on said needle connector means and on said plunger for coupling said plunger to said needle connector means in response to predetermined distal movement of said plunger;

vent passage means for connecting a space within said barrel distal of said plunger with a space proximal of said plunger;

means for normally closing said vent passage means;

means for opening said vent passage means in response to said predetermined distal movement of said plunger.

36. The syringe of claim 35 further comprising:

seal means on said plunger for closing said passage of said needle connector means during at least a portion of said predetermined distal movement of said plunger.

37. The syringe of claim 36 further comprising:

anchor means on said elastomeric member for retaining said needle connector means within said opening, said anchor means providing for release of said needle connector means from said elastomeric member in response to said predetermined distal movement of said plunger.

38. A syringe comprising:
a barrel;
a plunger slidable in said barrel;
needle connector means releasably retained in an opening at a distal end of said barrel and having needle passage means therethrough for connecting a needle cannula in fluid communication with said barrel;

coupling means on said needle connector means and on said plunger for coupling said plunger to said needle connector means in response to predetermined distal movement of said plunger; and seal means on said plunger for blocking said passage during said predetermined distal movement of said plunger.

39. A syringe comprising:
a rigid barrel having an open distal end;
a plunger slidable in said barrel;
an elastomeric member mounted at said distal end of said barrel and having an opening therethrough;
needle connector means positioned in said opening of said elastomeric member and having a passage therethrough for connecting a needle cannula in fluid communication with said barrel;

coupling means on said needle connector means and on said plunger for coupling said plunger to said needle connector means in response to predetermined distal movement of said plunger;

anchor means on said elastomeric member for retaining said needle connector means within said opening through said elastomeric member; and said anchor means providing for release of said needle connector means from said elastomeric member in response to said predetermined movement of said plunger to permit withdrawal of said needle connector means from said position in said opening of said elastomeric member to within said barrel.

40. The syringe of claim 39 further comprising:

vent passage means for connnecting a space within said barrel distal of said plunger with a space proximal of said plunger; and means for normally closing said vent passage and means for opening said vent passage in response to said predetermined distal movement of said plunger.

41. A retractable needle syringe comprising:
a barrel having a bore open at proximal and distal ends thereof;
a plunger reciprocally movable in said bore including a rod extending through the proximal open end of said bore;
resilient piston means connected to the distal end of said rod for slidably sealing said plunger against the wall of said bore;
needle connection means having a needle passage therethrough for connecting a cannula of a needle mounted on said needle connector means in fluid communication with said bore;
resilient elastomeric anchor means having an opening therethrough fixed on said barrel proximate the distal end thereof and extending through the distal open end of said bore for anchoring said needle connector within said opening;
said needle connector being releasably anchored in said opening of said anchor means and having radial abutment means thereon adjacent to the proximal end thereof;
said needle connector having a first coupling means adjacent the distal end thereof, and said plunger including second coupling means adjacent the distal end thereof complementary to said first coupling means, for coupling said plunger to said needle connector means upon coupling engagement of said second coupling means with said first coupling means in response to predetermined distal movement of said plunger;
said second coupling means including axially extending latching fingers connected to said rod at the distal end thereof, said latching fingers having portions movable over said abutments into latching engagement therewith to lock said rod to said needle connector means in response to said predetermined distal movement of said rod;
said plunger being movable in the proximal direction subsequent to said coupling engagement to release said needle connector form said anchor means and to move said needle connector into said barrel; and
said plunger including seal means for closing said needle passage during at least a portion of said predetermined distal movement of said rod, said seal means including an axially extending elastomeric plug extending distally of said resilient piston means so that during said further predetermined distal movement of said plunger said plug blocks said needle passage.

42. A retractable needle syringe comprising:
a barrel having a bore open at proximal and distal ends thereof;
a plunger reciprocally movable in said bore including a rod extending through the proximal open end of said bore;
resilient piston means connected to the distal end of said rod for slidably sealing said plunger against the wall of said bore;
needle connection means having a needle passage therethrough for connecting a cannula of a needle mounted on said needle connector means in fluid communication with said bore;
resilient elastomeric anchor means having an opening therethrough fixed on said barrel proximate the distal end thereof and extending through the distal open end of said bore for anchoring said needle connector within said opening;
said needle connector being releasably anchored in said opening of said anchor means and having radial abutment means thereon adjacent to the proximal end thereof;
said needle connector having a first coupling means adjacent the distal end thereof, and said plunger including second coupling means adjacent the distal end thereof complementary to said first coupling means for coupling said plunger to said needle connector means upon coupling engagement of said second coupling means with said first coupling means in response to predetermined distal movement of said plunger;
said second coupling means including axially extending latching fingers connected to said rod at the distal end thereof, said latching fingers having portions moveable over said abutments into latching engagement therewith to lock said rod to said needle connector means in response to said predetermined distal movement of said rod;
said plunger being movable in the proximal direction subsequent to said coupling engagement to release said needle connector form said anchor means and to move said needle connector into said barrel; and
said plunger including a vent passage extending between a space within said bore proximal of said resilient piston means, and a space within said bore distal of said resilient piston means, and valve means for normally closing said vent passage, said valve means being operable by movement of said rod to open said vent passage during said predetermined distal movement of said plunger.

43. The retractable needle syringe of claim 42 wherein said plunger includes seal means for closing said needle passage during at least a portion of said predetermined distal movement of said rod, said seal means including an axially extending elastomeric plug extending distally of said resilient piston means so that during said further predetermined distal movement of said plunger said plug blocks said needle passage.

44. A retractable needle syringe comprising:
a barrel having a bore open at proximal and distal ends thereof;
a plunger reciprocally movable in said bore including a rod extending through the proximal open end of said bore;
resilient piston means connected to the distal end of said rod for slidably sealing said plunger against the wall of said bore;
needle connection means having a needle passage therethrough for connecting a cannula of a needle mounted on said needle connector means in fluid communication with said bore;
resilient elastomeric anchor means having an opening therethrough fixed on said barrel proximate the distal end thereof and extending through the distal open end of said bore for anchoring said needle connector within said opening;
said needle connector being releasably anchored in said opening of said anchor means and having radial abutment means thereon adjacent to the proximal end thereof;

said needle connector having a first coupling means adjacent the distal end thereof, and said plunger including second coupling means adjacent the distal end thereof complementary to said first coupling means, for coupling said plunger to said needle connector means upon coupling engagement of said second coupling means with said first coupling means in response to predetermined distal movement of said plunger;

said second coupling means including axially extending latching fingers connected to said rod at the distal end thereof, said latching fingers having portions movable over said abutments into latching engagement therewith to lock said rod to said needle connector means in response to said predetermined distal movement of said rod;

said plunger being movable in the proximal direction subsequent to said coupling engagement to release said needle connector form said anchor means and to move said needle connector into said barrel;

said anchor means including an annular radially displacable anchor flange engaged with a radially extending anchor ring on said needle connector; and release means on said latching fingers for radially displacing said anchor flange from engagement with said anchor ring in response to said predetermined distal movement of said plunger.

45. The retractable needle syringe of claim 44 wherein said plunger includes seal means for closing said needle passage during at least a portion of said predetermined distal movement of said rod, said seal means including an axially extending elastomeric plug extending distally of said resilient piston means of that during said further predetermined distal movement of said plunger said plug blocks said needle passage.

46. The retractable needle syringe of claim 44 wherein said plunger including a vent passage extending between a space within said bore proximal of said resilient piston means, and a space within said bore distal of said resilient piston means and valve means for normally closing said vent passage, said valve means being operable by movement of said rod to open said vent passage during said predetermined distal movement of said plunger.

47. The retractable needle syringe of claim 46 wherein said plunger including seal means for closing said needle passage during at least a portion of said predetermined distal movement of said rod, said seal means including an axially extending elastomeric plug extending distally of said resilient piston means so that during said further predetermined distal movement of said plunger said plug blocks said needle passage.

* * * * *